(12) United States Patent
Woodham

(10) Patent No.: US 9,753,008 B2
(45) Date of Patent: Sep. 5, 2017

(54) GEL ELECTROPHORESIS AND TRANSFER COMBINATION USING CONDUCTIVE POLYMERS AND METHOD OF USE

(71) Applicant: Woodham Biotechnology Holdings, LLC, Beverly Hills, CA (US)

(72) Inventor: Andrew Woodham, Los Angeles, CA (US)

(73) Assignee: Woodham Biotechnology Holdings, LLC, Beverly Hills, CA (US)

( * ) Notice: Subject to any disclaimer, the term of this patent is extended or adjusted under 35 U.S.C. 154(b) by 0 days.

(21) Appl. No.: 15/348,803

(22) Filed: Nov. 10, 2016

(65) Prior Publication Data

US 2017/0131235 A1 May 11, 2017

Related U.S. Application Data

(63) Continuation-in-part of application No. 15/017,540, filed on Feb. 5, 2016, now abandoned.
(Continued)

(51) Int. Cl.
*G01N 27/447* (2006.01)
*G01N 27/453* (2006.01)

(52) U.S. Cl.
CPC . *G01N 27/44739* (2013.01); *G01N 27/44713* (2013.01)

(58) Field of Classification Search
CPC ....... G01N 27/44739; G01N 27/44782; G01N 27/453
See application file for complete search history.

(56) References Cited

U.S. PATENT DOCUMENTS 4,994,166 A 2/1991 Fernwood
5,102,524 A 4/1992 Dutertre
(Continued)

FOREIGN PATENT DOCUMENTS

EP 1632772 A1 3/2006
JP S6232145 A 2/1987
(Continued)

OTHER PUBLICATIONS

Li et al., "The Regulation of Osteogenesis Using Electroactive Polypyrolle Films," Polymers 2016, 8, 258, pp. 1-12.*
(Continued)

*Primary Examiner* — Alexander Noguerola
(74) *Attorney, Agent, or Firm* — Trojan Law Offices

(57) ABSTRACT

A precast gel and membrane combination unit for use in gel electrophoresis and membrane transfer for protein analysis, and method of use. Transparent electrically conductive polymer plate(s) house an electrophoresis gel and immunoblotting membrane. The gel and membrane are positioned between two plates of conductive polymers or plates having an electrically conductive layer or film. During the electrophoresis step, electric current moves proteins through the gel allowing for protein separation. Then, without removing or reorienting the gel or apparatus, the electrical contacts are switched to allow the flow of electricity to run perpendicularly through the gel via the conductive polymers, which will allow the proteins to transfer to the membrane housed in the same precast gel and membrane combination unit. The apparatus allows the user to visualize the steps of protein separation and protein transfer without transferring the gel between electrophoresis and transfer steps.

18 Claims, 8 Drawing Sheets

Related U.S. Application Data

(60) Provisional application No. 62/253,143, filed on Nov. 10, 2015.

(56) References Cited

U.S. PATENT DOCUMENTS

| | | | |
|---|---|---|---|
| 5,449,446 | A | 9/1995 | Verma |
| 5,593,561 | A | 1/1997 | Cognard |
| 6,602,391 | B2 | 8/2003 | Serikov |
| 7,118,836 | B2 | 10/2006 | Andriessen |
| 7,427,441 | B2 | 9/2008 | Majumdar |
| 7,645,369 | B2 | 1/2010 | Hoeltke |
| 8,029,657 | B1 | 10/2011 | Wu |
| 8,048,709 | B2 | 11/2011 | Bandera |
| 8,173,002 | B2 | 5/2012 | Margalit |
| 8,702,950 | B2 | 4/2014 | Maruo |
| 8,922,435 | B2 | 12/2014 | Fontecchio |
| 2003/0032201 | A1 | 2/2003 | Flesher |
| 2004/0033369 | A1 | 2/2004 | Fleming |
| 2006/0042951 | A1 | 3/2006 | Ohse |
| 2006/0187527 | A1 | 8/2006 | Komatsu |
| 2007/0284250 | A1 | 12/2007 | Magnant |
| 2010/0044229 | A1 | 2/2010 | Margalit |
| 2010/0247870 | A1 | 9/2010 | Suzuki |
| 2011/0151201 | A1 | 6/2011 | Lee |
| 2012/0190591 | A1 | 7/2012 | Wohlstadter |
| 2013/0115714 | A1 | 5/2013 | Macnamara |
| 2013/0168126 | A1 | 7/2013 | Kuchta |
| 2014/0131205 | A1 | 5/2014 | Margalit |

FOREIGN PATENT DOCUMENTS

| | | |
|---|---|---|
| JP | H06192471 A | 7/1994 |
| WO | PCT/IB01/02234 A1 | 6/2003 |
| WO | WO2009131257 A1 | 10/2009 |
| WO | WO2010135364 A2 | 11/2010 |
| WO | WO2011106693 A2 | 9/2011 |
| WO | WO2012027219 A1 | 3/2012 |
| WO | WO2014016194 A1 | 1/2014 |

OTHER PUBLICATIONS

Yavuz et al., "Polypyrrole composites for shielding applications," Synthetic Metals 151 (2005) 211-217.*

Silva et al., "Electrochromic Properties of Polyaniline-Based Hybrid Organic/Inorgainc AMterials," J. Braz. Chem. Soc., vol. 27, No. 10, 1847-1857, 2016.*

Ikenoue et al., "Fabrication of conducing poly(3,4-ethylenedioxythiophen):poly(styrenesulfonate) thin films by ultrasonic spray-assisted mist deposition method," Thin Solid Films 520 (2012) 1978-1981.*

Rahman et al., "ITO-free low-cost organic cells with highly conductive poly(3,4 ethylenedioxythiophene): p-tolunene sulfonate anodes," Solar Energy Materials & Solar Cells 95 (2011) 3573-3578.*

Aronggaowa et al., "Thin, transparent conductive films fabricated from conducting polymer nanofibers", Polymer Journal (2013) 45, 819-823.*

Murat Ates, Tolga Karazehir, A. Sezai Serac, "Conducting polymers and their applications." Current Physical Chemistry 2.3 (2012): 224-240.

M. Omastova et al, "Surface Characterization of Conductive Poly(metyl methacrylate)/Polypyrrole Composites," Journal of Materials Science 35 (2000) 1743-1749.

Zhang et al., "A Nanocellulose Polypyrrole Composte Based on Tunicate Cellulose," International Journal of Polymer Science, vol. 2013, Article ID 175609.

Xu et al., "Synthesis and Characterization of Nanosized Polypyrrole Polystyrene Composite Particles," Journal of Applied Polymer Science, vol. 91, 1360-1367 (2004).

Yavuz et al., "Polypyrrole composites for shielding applications," Synthetic Metals 151 (2005) 211-217).

Cakmak et al., "Flexible and Conducting Composites of Polypyrrole and Polydimethylsiloxane," Journal of Applied Polymer Science, vol. 93, 736-741 (2004).

Eisazadeh, "Studying the Characteristics of Polypyrrole and its Composites," World Journal of Chemistry 2 (2: 67-74, 2007).

Pirvu et al., "Characterization of Conductive Poly(Acrylonitrio-co-Vinyl Acetate Composites: Matrix Polymerization of Pyrrole Derivatives," Fibers and Polymers 2011, vol. 12, No. 2, 151-158.

Ferenets et al., "Chemical in situ polymerization of polypyrrole on poly(methyl metacrylate) substrate," Thin Solid Film 515 (2007) 5324-5328).

Silva et al. "Electrochromic Properties of Polyaniline-Based Hybrid Organic/Inorganic Materials," J. Braz. Chem. Soc., vol. 27, No. 10, 1847-1857, 2016.

Malti et al., "An Organic Mixed Ion-Electron Conductor for Power Electronics," Advanced Science 2016, 3, 1500305.

Li et al., "Conductivity decay of cellulose-polypyrrole conductive paper composite prepared by in situ polymerization method." Carbohydrate Polymers 82 (2010) 504-509.

International Search Report and Written Opinion for Equivalent PCT application that claims priority to the present application; dated Feb. 2, 2017; Int. Application No. PCT/US16/61443.

Shian et al., "Tunable lenses using transparent dielectric elastomer actuators," Optical Society of America, 2013, vol. 21, No. 7.

Schewe and Rost, "Conductive, Transparent, Flexible, Poly-IC; Kunstoffe International"; Oct. 2012; www.kunstoffe-international.com.

Savagatrup et al., "Plasticizatoin of PEDOT:PSS by Common Additives for Mechanically Robust Organic Solar Cells and Wearable Sensors"; (2012) Advanced Functional Materials; vol. 25, pp. 427-536.

Aronggaowa et al., Transparent Conductive Films Fabricated from Polythiophene Nanofibers Composited with Conventional Polymers, Polymers, 2013, vol. 5, pp. 1325-1338.

Kim et al., Highly conductive and transparent Poly(3,4-ethylenedioxythiophene):p-Tolunene Sulfonate Films as a Flexible Organic Electrode; Japanese Journal of Applied Physics 48 (2009); 091501.

Chen et al., Characterization of an electroactive polymer for overcharge protection in secondary lithium batteries; Electrochimica Acta, 2005, vol. 50, pp. 4666-4673.

Wan et al., 3D Conducting Polymer Platforms for Electrical Control of Protein Conformation and Cellular Functions; J. Mater. Chem. B., 2015, vol. 3(25), pp. 4050-5048.

Ji et al., Thermal Response of Transparent Silver Nanowire/PEDOT:PSS Film Heaters; Small; 2014; 10, No. 23, 4951-4960.

Wayback Machine Archive of Website "Clear Conductive Polycarbonate Sheet for Carrier Tape"; http://www.evacutech.com.tw:80/products/p_c_pc_film_en.html; Mar. 28, 2014.

Wayback Machine Archive of Website "Thermoform Clear Conductive PET Sheet"; http://www.evacutech.com.tw:80/products/p_c_apet_sheet_en.html; Mar. 28, 2014.

Xu et al., A Novel dielectric elastomer actuator based on polyvinyl alcohol hydrogel compliant electrodes. (2014) arXiv preprint, arXiv:1409.2611.

Worfolk et al., "Ultrahigh electrical conductivity in solution-sheared polymeric transparent films," (2015) PNAS; vol. 112, No. 46, pp. 14138-14143.

* cited by examiner

GEL ELECTROPHORESIS AND TRANSFER COMBINATION USING CONDUCTIVE POLYMERS AND METHOD OF USE

CROSS REFERENCE TO RELATED APPLICATIONS

This application is a continuation-in-part of U.S. application Ser. No. 15/017,540, filed Feb. 5, 2016, which claims the benefit of U.S. Provisional Patent Application No. 62/253,143, filed on Nov. 10, 2015, which are both hereby incorporated by reference herein.

FIELD OF THE INVENTION

The present invention relates generally to gel electrophoresis and transfer of macromolecules, and more specifically to using a single precast gel and membrane combination unit having transparent conductive polymers.

BACKGROUND OF THE INVENTION

Although western blotting is a common technique, there are still many issues that arise from the transferring step. These include the introduction of air bubbles when placing gels on membranes, and as gels have become thinner to reduce the amount of protein needed, the tearing of gels the occurs when the user moves the gels from the precast setting to the blotting membrane. These complications can be devastating when the analysis of limited amounts of protein is required, especially when no more protein is available or it is a clinical specimen. Furthermore, the concept of a protein separation and transfer combination unit is hindered by the current use of insulating plastics to house precast gels. Additionally, researchers often prefer to watch protein separation during electrophoresis, which limits the use of nontransparent materials as the gel supporting structural plates.

Simplifying the western blotting technique reducing the traditional two step process (protein separation and protein transfer) into a single step and using a single apparatus instead of separate apparatuses for electrophoresis and for protein transfer. However, one challenge in creating a single combination gel electrophoresis and protein transfer unit involves creating an apparatus where the user can visualize the degree of protein separation during electrophoresis and thereafter transfer the proteins to a blotting membrane without physically transferring the gel to the membrane. For such an apparatus to perform both electrophoresis and protein transfer, the plates must form the structural support for the gel, but also be able to transfer current through the gel supporting plates to the blotting membrane. The challenge is that the electrical current required to transfer proteins to the blotting membrane must run perpendicularly to the current required to separate proteins during electrophoresis.

There have been many attempts to simplify the separation and transfer of proteins and other macromolecules using various apparatuses and techniques. U.S. Pat. No. 4,994,166 to Fernwood et al. describes a single apparatus for slab gel electrophoresis and blotting, both of which are performed in a single tank cell having separation electrodes along opposing vertical walls, and blotting electrodes arranged horizontally above and below the level of the gel. The cell is operated in separatory and blotting modes, in which separatory and blotting electrodes are separately energized. Fernwood requires porous gel supports to allow the electric field to pass through the membrane and the top plate transfer electrode must be removed from contact with the buffer solution during the separatory phase. Fernwood also discusses some of the problems of using gel-supporting plates for both electrophoresis and transfer of proteins. Since there must be a potential difference sustained between the two ends of the gel during separation phase, conductive blotting electrodes in contact with the buffer solution during separation nullify the field around the gel, thereby preventing protein migration and separation. Fernwood solves this problem by using a wire array as the lower blotting electrode, and in order to avoid the nullifying field, the electrode must either be raised above or lowered below the liquid buffer level in the tank. Another solution offered is that the height of the electrode plate may be fixed, and the buffer level raised and lowered as necessary to establish or break electrical contact with the gel supporting plate. Raising or lowering the plate or buffer between electrophoresis and transfer phases requires an additional level of complexity to the apparatuses and methods for separating transferring proteins to a blotting membrane.

U.S. Pat. No. 5,102,524 to Dutertre describes an electrophoresis device and method to control migration of macromolecules through gel plates, where different sets of electrodes are used in a two-step process to first separate macromolecules (e.g. proteins) and then to transfer the molecules to a blotting membrane.

U.S. Pat. No. 5,593,561 to Cognard also describes an electrophoresis device and method for controlled migration of macromolecules and transfer thereof to a membrane in a vessel. The first electric field, established between electrodes, provides means for macromolecular separation in a gel, and the second electric field, perpendicular to the first, provides means for transferring the macromolecules onto the membrane. In the described method, electrodes and blotting membranes are assembled in the vessel, which is then filled with gel. The gel is then liquefied, allowing the removal of the membrane. Cognard's device is for use without a prefabricated gel and membrane unit.

U.S. Pat. No. 8,173,002 to Margalit discloses a dry blotting system to transfer proteins onto a blotting membrane. The system does not include an electrophoresis device, so the device does not allow the user to visualize separation and blotting of proteins in a single device. The device requires the user to be present to transfer the gel to a blotting membrane on the blotting device. Margalit teaches the use of electrically conducting polymers, but not in combination with a single device that can both separate proteins and transfer the proteins to a blotting membrane. Margalit does not teach the use of transparent gel supporting plates so that the user can visualize protein separation during electrophoresis.

U.S. Patent Appl. Pub. No. 2006/0042951 to Ohse discloses an apparatus to separate and transfer proteins via the use of a fine grove, a transferring electrode and a transparent conductive material having a thickness of approximately 0.1 $\mu$m. The apparatus includes a pair of separating electrodes for causing a substance in a sample to move along a passage, and a pair of transferring electrodes for causing the substance in the sample to be transferred to the capturing material by electrophoresis. The transparent conductive material is not capable of being the support structure due to its thickness of approximately 0.1 $\mu$m, which would not have sufficient rigidity to serve as the supporting walls for a gel. The separation and blotting is performed in an electrophoresis buffer and does not make use of a gel slab or gel slab assembly, which are commonly used for western blots.

U.S. Pat. No. 6,602,391 to Serikov discloses an apparatus and method for capillary separation of macromolecules and post-separation blotting. However, Serikov does not disclose the use of a slab gel where the user can view the separation of macromolecules and transfer the macromolecule to a blotting membrane for western blotting.

Conductive polymers have previously been described, but not in conjunction with electrophoresis and blotting. Ates et al. describes numerous applications of conducting polymers in "Conducting Polymers and their Applications" (Current Physical Chemistry, 2012, 2, 224-240). International Patent Application No. PCT/EP2013/065163 to Jung discloses a conductive polymer composition and transparent electrode for an antistatic layer. International Patent Application No. PCT/KR2008/002236 to Kim discloses a conductive polymer for use as a transparent electrode and the method of fabricating the electrode using an ink jet spray method. U.S. patent application Ser. No. 13/616,804 discloses a transparent panel and method of manufacturing a transparent panel where a conductive polymer layer is formed to make a transparent electrode.

Transparent conductive plates using conductive polymers have not been used in electrophoresis and blotting apparatuses where the conductive plates are used as both the gel supporting structures so that the pre-cast gel and its conductive polymer housing can be used for both electrophoresis and blotting without removing the gel after protein separation and still be used as the gel supporting structure as the proteins are transferred to the blotting membrane.

There currently remains a need for devices and associated methods that can perform gel electrophoresis and protein transfer in a single precast gel and membrane combination unit. Additionally, since researchers prefer to watch the electrophoresis steps during the electrophoresis phase, there remains a need develop gel structural supporting plates that allow visualization, but can also be used in both the electrophoresis phase and protein transfer phase of a western blot.

All patents, patent applications, and non-patent applications disclosed in the background and description of the invention are hereby incorporated by reference for all purposes in their entireties.

SUMMARY OF THE INVENTION

The present invention advantageously fills the aforementioned deficiencies by providing gel electrophoresis and transfer with one precast gel and membrane combination unit using conductive polymers, which provides a fast, reliable, and easy method to perform a hands-free protein separation followed by an efficient transfer of proteins to a blotting membrane.

The technology is defined as any technology, invention, know-how, method, composition, device, machine, product, consumable, formula and any combination thereof that relates to any use of conductive, semiconductive, and/or dissipative materials in the structure of a device for supporting an electrophoretic gel in which a blotting membrane is positioned adjacent to the gel, thereby permitting electrical current to flow through the gel in one direction during the protein separation phase and after the protein separation phase has completed, the current flows through a conductive plate or semi-conductive plate in a direction perpendicular to the direction of the flow of the current during the separation phase. This is accomplished without removing the gel from the precast gel and membrane combination unit.

The invention includes a method for gel electrophoresis and protein transfer in a precast gel and membrane combination unit. The precast gel and membrane combination unit consists of conductive/semi-conductive polymer casings, an electrophoresis gel, and blotting membrane for use in a western blot. The gel and membrane pair is sandwiched between two sheets of the conductive polymer. The gel is capable of separating proteins by size within the gel when an electric current flows between electrodes on opposite sides of the y-axis of the gel. The blotting membrane is capable of immobilizing proteins transferred from the gel after protein separation without physically transferring the gel to the blotting membrane after protein separation.

The present invention may also include one or more of the following: a thin layer of a less conductive gel (i.e. high percentage polyacrylamide) between the gel and the membrane; different types of electrophoresis gels including those made from polyacrylamide, bis-Tris, Tris-acetate, etc.; different immunoblotting membranes including those made from nitrocellulose, and polyvinylidene difluoride (PVDF); different conductive polymer materials; plastic insulators; a buffer tank and buffer lid; precast gel and membrane holder cassette with electrodes; negative electrode chamber; positive electrode chamber; electrode assembly; anode and cathode buffers; cooling unit; and a programmable power source.

The present invention is unique in that it utilizes innovative conductive polymers with particular resistivity in western blotting applications to solve fundamental problems in current methods, and that allows for convenient, one-step electrophoresis and transfer methods. More specifically, the present invention owes its uniqueness to the fact that it utilizes conductive/semi-conductive polymers to house a precast gel and blotting membrane combination which acts as an insulator in one scenario (electrophoresis) and an electrode in another scenario (protein transfer), which is advantageous for a device that separates proteins by size in one direction using one pair of electrodes and transfers proteins in a perpendicular manner to a blotting membrane through the use of a different pair of electrodes. The conductive polymers used to structurally support the pre-cast gel are transparent, which allows the user to visualize protein separation during electrophoresis.

It is an object of the present invention to provide gel electrophoresis and transfer with one precast gel and blotting membrane combination unit using conductive polymers that does not suffer from any of the problems or deficiencies associated with prior solutions.

In one embodiment there is an apparatus for electrophoretic separation and blotting. The apparatus has a first electrically semi-conductive plate made from a transparent conductive polymer and a second electrically semi-conductive plate substantially parallel to the first electrically semi-conductive plate. The apparatus has an electrophoresis gel and a blotting membrane where the electrophoresis gel is located between the first electrically semi-conductive plate and the blotting membrane. The blotting membrane is between the electrophoresis gel and the second electrically semi-conductive plate.

In another embodiment, the apparatus also includes a low conductivity (high resistivity) gel between the second electrically semi-conductive plate and the blotting membrane. The embodiment also includes filter paper between the second electrically semi-conductive plate and the blotting membrane.

In yet another embodiment, the first transparent electrically conductive plate has electrically conducting wires arranged in an array or grid to disperse current/charge throughout the plate.

In yet another embodiment, the first plate is generally formed from a non-electrically conductive static-dissipative material. The apparatus has a first plate made from a transparent polymer, an electrically semi-conductive transparent layer adjacent to the first plate, a second plate substantially parallel to the first plate, an electrophoresis gel and a blotting membrane. In this embodiment, the non-electrically conductive static-dissipative plate has a thin transparent electrically conductive polymer layer or thin transparent electrically conducting film disposed at least the first plate's inner surface to act as a plate electrode during the blotting phase, but acts an insulating plate during electrophoresis.

In yet another embodiment, the apparatus includes a liquid receptacle tank having an upper buffer chamber and lower buffer chamber each with a separation phase electrode. The tank also has a pair of blotting phase electrodes arrange in a manner so that the electric field produced from the separation phase electrodes is substantially perpendicular to the electric field produced from the blotting phase electrodes. The apparatus also includes a power supply configured to automatically or manually switch between, and apply, a voltage to the separation phase electrodes, and a voltage to the blotting phase electrodes after the separation of proteins step.

In yet another embodiment, there is a method for separation and post-separation blotting of macromolecules to a blotting membrane. The user provides an apparatus in a first orientation within a liquid receptacle tank. The apparatus has a first electrically semi-conductive plate comprised of a transparent conductive polymer, a second electrically conductive plate substantially parallel to the first electrically conductive plate, an electrophoresis gel, and a blotting membrane. The electrophoresis gel is located between the first conductive plate and the blotting membrane, and the blotting membrane is located between the electrophoresis gel and the second electrically conductive plate. The user separates the macromolecules (e.g. proteins) along the gel of the apparatus by applying a first electrical driving force to a pair of separation electrodes, which causes current to flow along the y-axis of the gel. The voltage causes the separating of biomolecules within the gel by size, that is, larger molecules migrate slower along the y-axis than smaller molecules. The electrical force applied to the separation electrodes is then discontinued. Without removing the gel and transfer membrane from the liquid receptacle tank, and also while maintaining the same orientation of the gel and membrane in the liquid receptacle tank, a second electrical driving force is applied to a pair of blotting electrodes substantially perpendicular to the first electrical driving force. The orientation of the gel and membrane unit is maintained relative to both the separation and blotting electrodes. The second electrical driving force causes current to flow along a z-axis of the gel in the first orientation. The second electrical driving force transfers biomolecules from the gel to a blotting membrane adjacent to the gel. The steps of separating the biomolecules and transferring the biomolecules to the blotting membrane are performed without removing the unit from the tank, thereby combining the steps of electrophoresis and transfer of proteins to the blotting membrane in a single liquid receptacle tank without having to reorient the gel and membrane combination unit between the separating step and transferring step.

The present invention now will be described more fully hereinafter with reference to the accompanying drawings, which are intended to be read in conjunction with both this summary, the detailed description, and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete, and will fully convey the full scope of the invention to those skilled in the art.

BRIEF DESCRIPTION OF THE DRAWINGS

These and other features and advantages of the present invention will become appreciated as the same becomes better understood with reference to the specification, claims, and drawings herein:

DETAILED DESCRIPTION OF THE DRAWINGS

Figure 1:
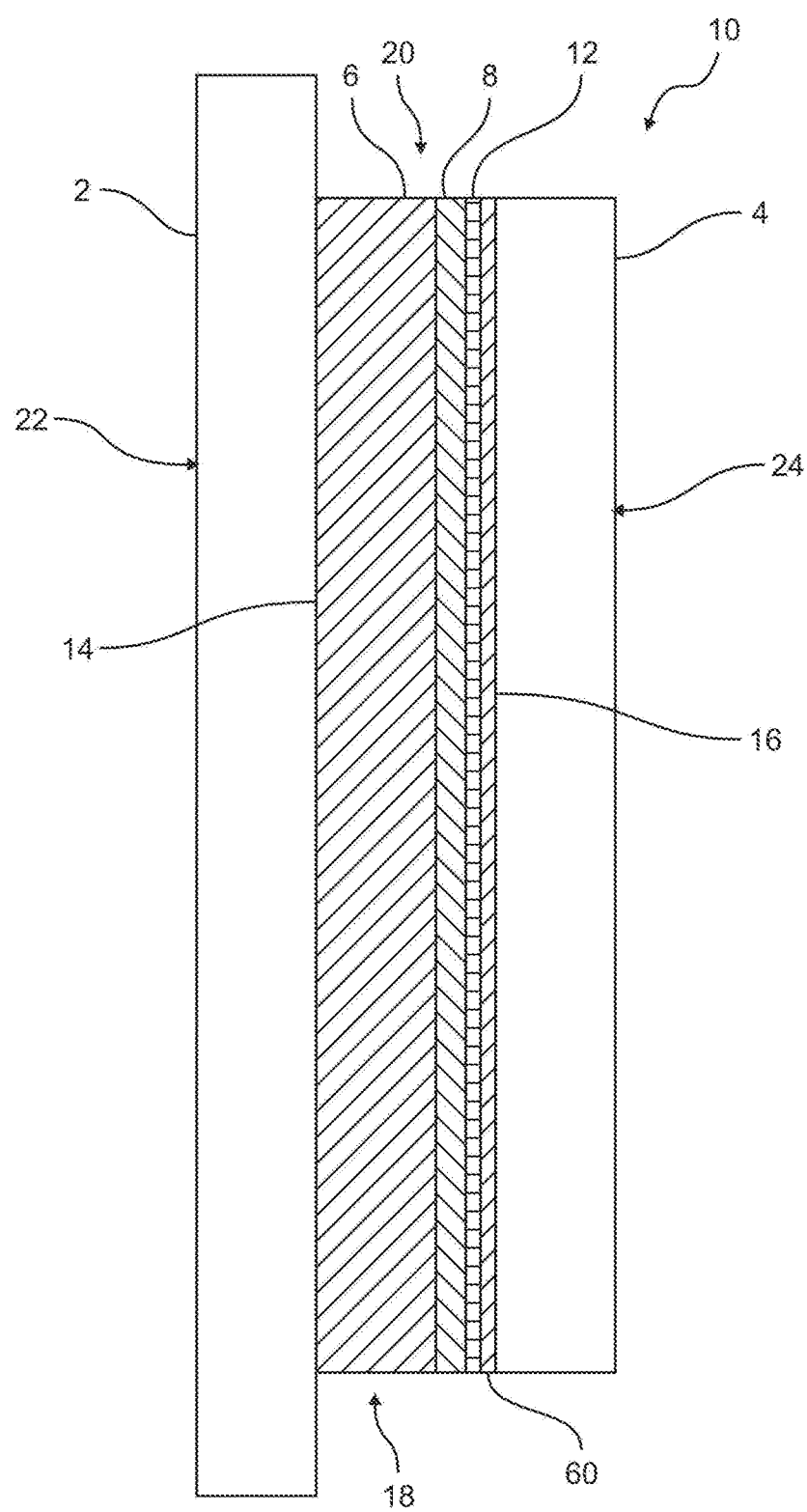
FIG. 1 shows a side view of the general setup of the precast gel and membrane combination unit for electrophoresis and transfer.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," "left" or "right," may be used herein to describe one element's relationship to another element(s) as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. The invention illustratively disclosed herein suitably may be practiced in the absence of any elements that are not specifically disclosed herein.

The present invention is directed to gel electrophoresis and transfer with one precast gel and membrane combination unit 10 using conductive polymers. Electrophoresis may be performed using a variety of methods, including but not limited to sodium dodecyl sulfate polyacrylamide gel electrophoresis (SDS-PAGE).

In one embodiment, the invention is made of the following components: a precast gel and membrane combination unit 10 that includes the gel 6 and transfer/blotting membrane 12 sandwiched between two sheets of conductive polymers 2, 4. Additionally, a gel having low conductivity 8 separates the gel 6 and membrane 12.

FIG. 1 shows a side view of one embodiment of the general setup of the precast gel and membrane combination unit 10 for electrophoresis and transfer. Generally, a gel 6 and membrane 12 are sandwiched between two semi-conductive plates or sheets 2, 4 comprised of conductive/semi-conductive polymers. Additionally, the gel 6 and membrane 12 may be separated by a thin layer of a low conductive (i.e. high percentage polyacrylamide) gel 8. During separation mode, current flows from the upper surface 20 of the gel 6 to the lower surface 18 of the gel 6. During blotting mode (i.e. protein transfer mode), current flows from the first semi-conductive plate 2 to the second semi-conductive plate 4.

The first semi-conductive plate 2 is made from a transparent conductive material. These conductive materials include compositions of polyanilines, polypryrrols, polythiophenes, or other transparent conductive polymers more fully described below. The first conductive plate 2 has an outer surface 20 and inner surface 14. The second conductive plate 4 is also made from a conductive material, but need not be transparent because the user can visualize protein migration by just viewing one side of the gel. The advantage in using a system that includes a transparent conductive material instead of a non-transparent conductive material is that users often prefer to watch the separation phase of electrophoresis in order to visually determine the extent of protein movement/separation during electrophoresis. Typical plate electrodes are metal and therefore non-transparent. However, if typical metal plate electrodes are used along the surface of a gel, users cannot determine to what extent proteins have separated during electrophoresis. In one embodiment, only a single conductive plate 2 needs to be transparent for the user to visually determine how much protein movement has occurred because protein movement can be observed by looking at one side of a gel. The second side of the gel 6 will be blocked from view by the transfer/blotting membrane 12. In a preferred embodiment, the polymer used for the conductive plate 2 has a volume resistivity in the range of $10^3$-$10^5$ ohm-cm, but may be as high as $10^8$ ohm-cm. Plates 2, 4 can be a variety of sizes to support a gel. Typical gel supporting plates are around 10 cm×10 cm, but plates can be any size to accommodate a gel.

Using plates having a volume resistivity in the $10^3$-$10^5$ ohm-cm range or higher prevents electric field nullification when a current is applied to electrodes near the vertical ends of the gel because the plates have a higher volume resistivity than that of the electrophoresis gel (typically between 10-300 ohm-cm) that the plates 2, 4 surround. A nullifying electric field is prevented because current takes the path of least resistance and travels from the top separation electrode, through the gel, to the bottom separation electrode without causing the semi-conductive plates 2, 4 to emit a nullifying electric field.

Generally, the polymers used to create support structures for electrophoresis gels are polymers, and therefore electrically insulating. However, there is a special class of polymers that intrinsically conduct electricity at levels much higher than semiconductors (up to 1000 S/cm), and their conductivities/resistivities can be controlled through different methods of production. Conductive polymers are organic polymers that conduct electricity. Specifically, they offer electrical conductivity less than metals, and can have properties of plastics, such as transparency. The electrical properties (i.e. resistivity) can be fine-tuned using organic synthesis methods and dispersion techniques. Types of organic conductive polymers include polyacetylene, poly(pyrrole)s (PPY), polyanilines, poly(thiophene)s (PT), poly(3,4-ethylenedioxythiophene) (PEDOT), poly(p-phenylene sulfide) (PPS), poly(acetylene)s (PAC), poly(p-phenylene vinylene) (PPV), and their derivatives. Conductive polymers may be made from combinations of conductive polymers or combinations of derivatives of the polymers and combination of conductive polymers with non-conductive polymers. Generally, the electrical conductivity of a polymer is created by removing an electron from the polymer's conjugated π-orbital via doping and the delocalization of electrons along the polymer backbone.

To ensure that an electric field is evenly distributed along the entirety of the conductive plates, the composition of the plates should have high static-dissipative properties. To ensure a substantially equal electric field emanating from all regions of each conductive plate, the outer surface of a conductive plate may have one or more thin electrically conducting wires (or nanowires) disposed on or within the first electrically semi-conductive plate. The wires may be arranged in an array or grid-like shape or mesh. The wires are unobtrusive so that they do not prevent the user from being able to see the gel through the wires and conductive plate in order to allow the user to monitor protein separation during electrophoresis. Preferred embodiments having wires or grids of wires spaced between 0.5 cm and 1.0 cm apart may be sufficient to create a plate electrode having a substantially even electric field emanating from its surface.

Referring again to FIG. 1, adjacent to the inner surface 14 of the first conductive plate 2 is an electrophoresis gel 6. The electrophoresis gel 6 is a typical slab gel. The gel 6 may be made from any number of compositions known in the art, including agarose, polyacrylamide, Tris-glycine, bis-Tris, and Tris-acetate. Agarose gels would typically be used for DNA and RNA analysis and polyacrylamide gels, Tris-glycine, bis-Tris, Tris-acetate for protein analysis. Typical resolving gels for protein analysis are made between 6% and 15% polyacrylamide. In preferred embodiments, a bis-Tris gel is in a range of 10% to 12% and a Tris-acetate gel is in a range of 7%-10%, but values may lie outside these ranges depending on the size of the protein that one wishes to analyze or probe in the sample. For example, the smaller the known weight of a macromolecule, the higher the percentage of gel should be used. The dimensions of the electrophoresis gel 6 are typically rectangular and in a preferred embodiment are approximately 10 cm×10 cm, but may vary depending on the number of samples to be run simultaneously, the type of sample, and the sample volume. In a preferred embodiment, the precast gel and membrane combination unit 10 is less than 1 cm thick, but may also be designed thicker. On the opposing side of the electrophoresis gel 6 is a low conductivity (i.e. high percentage) gel 8.

Adjacent to the low conductivity gel 8 is a transfer membrane 12. The transfer membrane, also known as an immobilization membrane, may be of any of a wide range of blotting materials, such as blotting paper, nitrocellulose, PVDF, nylon, and other materials, as well as such materials in treated or derivatized form, as well known among those skilled in the art. The use of the membrane 12, and method by which the macromolecules are transferred from the electrophoresis gel 6 through the low conductivity gel 8 to the membrane 12 is discussed in further detail below. The low conductivity gel 8 between the transfer membrane 12 and electrophoresis gel 6 prevents the direct contact of the transfer membrane 12 with the electrophoresis gel 6 during electrophoresis. Since proteins have a high affinity to western blot transfer membranes 12, the low conductivity gel 8 prevents proteins from binding to the surface of the membrane 12 during electrophoresis.

Adjacent to the transfer membrane 12 is filter paper 60. The filter paper 60 is sandwiched between the high conductive gel 8 and second conductive plate 4. Filter paper 60, when wet, acts as an ion reservoir, thereby aiding in the transfer of macromolecules to the membrane 12. Filter paper also ensures that the transfer membrane 12 stays wet. The transfer membrane 12 and filter paper 60 may be pre-wet prior to assembly of the gel and membrane combination unit 10 with a methanol solution, other wetting buffer, or the filter paper 60 may be wet from the buffer solution used in the electrophoresis and blotting phases. A transfer membrane-wetting buffer typically includes methanol.

The gel and membrane combination unit 10 of FIG. 1 includes the electrophoresis gel 6, low conductivity gel 8, transfer membrane 12, and filter paper 60, all sandwiched between the transparent first conductive plate 2 and second conductive plate 4. Embodiments without the low conductivity gel 8 and/or filter paper 60 may also serve to both separate macromolecules and transfer the macromolecules to the transfer membrane 12.

Figure 2:
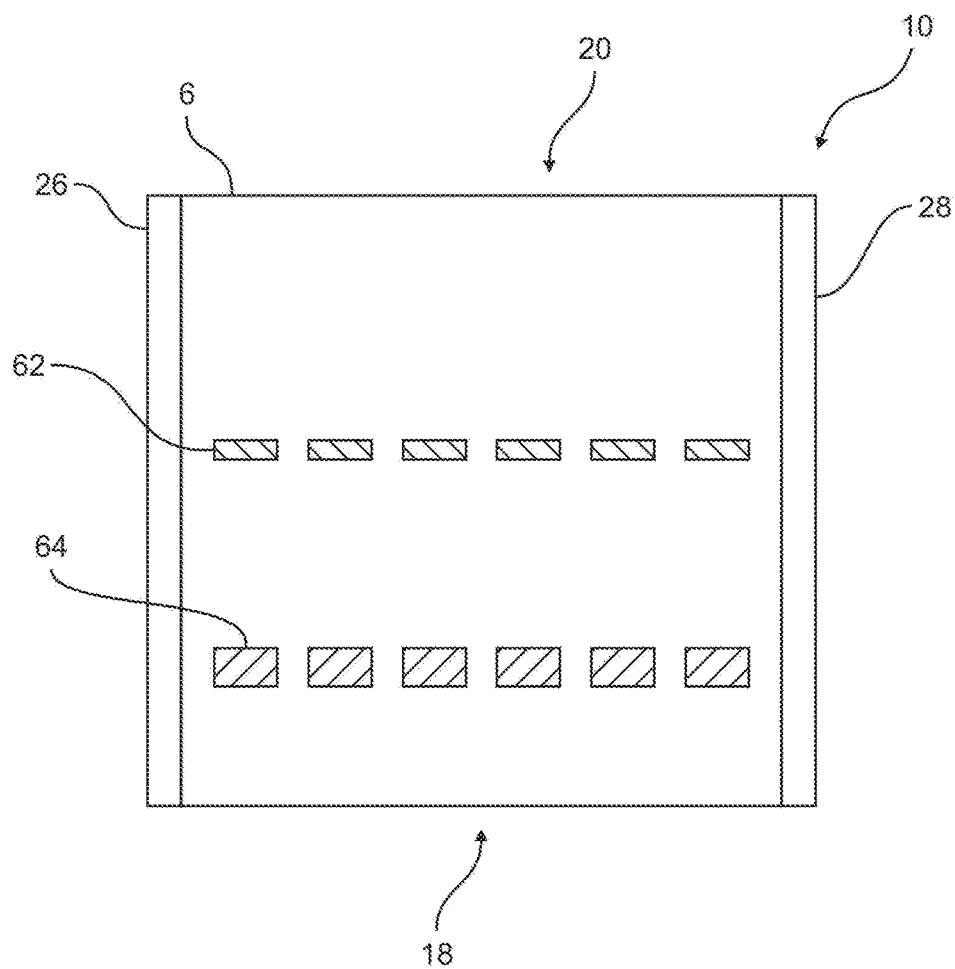
FIG. 2 shows a front view of a typical precast gel and membrane combination unit typically used for electrophoresis as known in the prior art.

FIG. 2 shows the front view of the precast gel and membrane combination unit 10 for electrophoresis and protein transfer. During the electrophoresis separation phase, proteins move vertically down from the top of the gel 20 to the bottom of the gel 18. During electrophoresis, larger proteins (shown as upper bands 62) move slower trough the gel 6 than smaller proteins (shown as lower bands 64). In one embodiment, there are two non-conductive insulative plastic strips 26, 28 that flank the sides of the gel 6, but that are also sandwiched between the conductive plastic/polymer sheets 2, 4 to direct current through the gel 6 during the electrophoresis step. These strips also provide structural support and rigidity to the cassette. The movement of the proteins during the transfer/blotting step is along the z-axis, perpendicular to the to the direction of protein separation along the y-axis.

Figure 3:
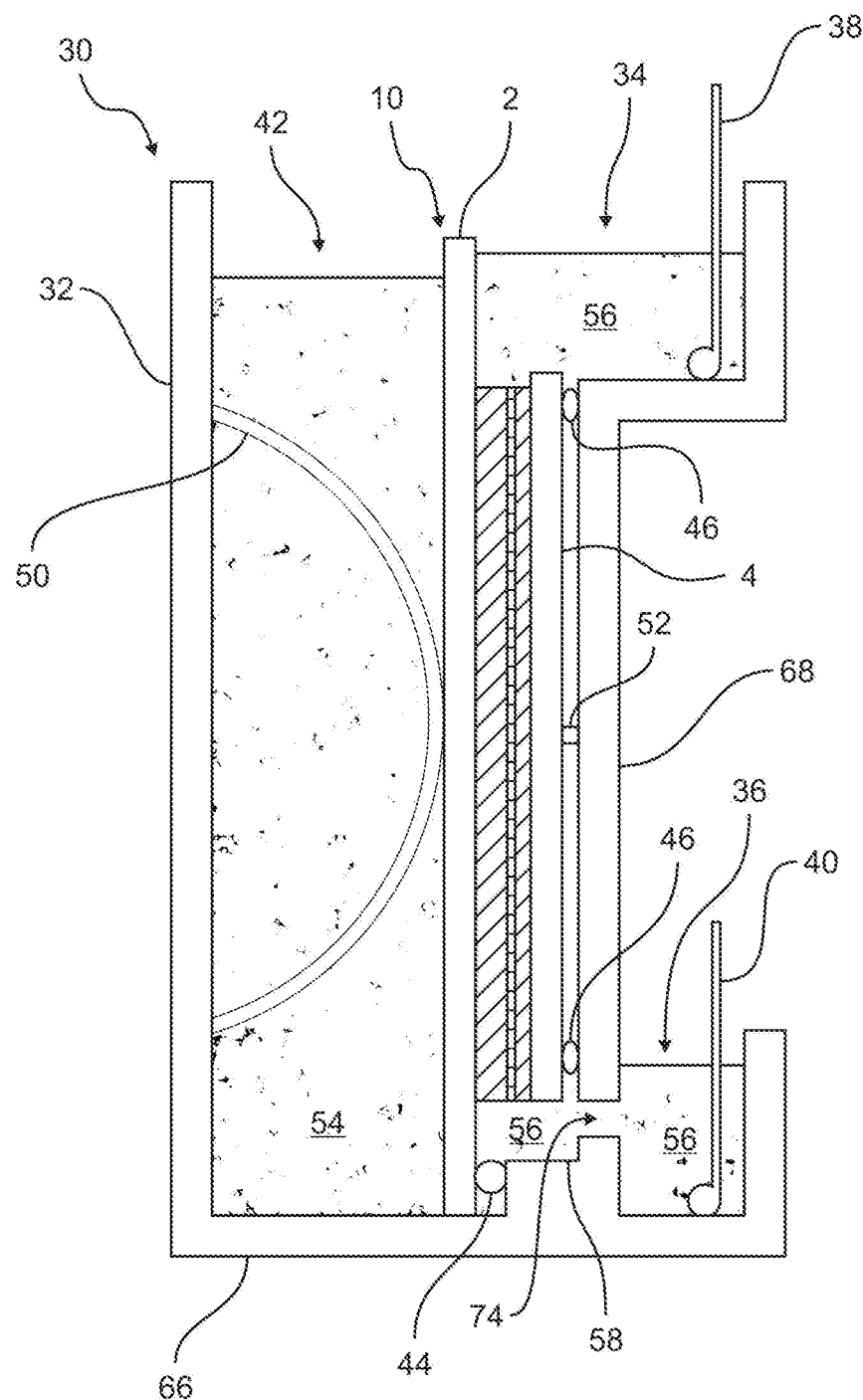
FIG. 3 shows a cross sectional side view of the of the precast gel and membrane combination unit within an electrophoresis and transfer tank.

The tank apparatus 30 of FIG. 3, which together with the precast gel and membrane combination unit 10, serves as the system for both the electrophoresis separation phase and transfer phase. The tank apparatus 30 is a liquid receptacle that includes a front panel 32, rear panel 68, first side panel 70, second side panel 72, bottom panel 66, lip 58 on the rear panel 68, and a lid (not shown). The lip 58 may be a variety of shapes but in a preferred embodiment is substantially U-shaped along the inner walls of the first and second side panels 70, 72 of the tank apparatus 30.

Gels for protein separation and transfer are usually submerged in an electrolyte containing buffered solution such as Tris-acetate-EDTA (TAE) buffer in a tank apparatus 30. Other buffers may be used depending on the type of gel used in the precast gel/membrane combination unit 10. For example, a Tris-acetate buffer may be used for Tris-acetate gels, whereas 2-(N-morpholino)ethanesulfonic acid (MES) or 3-(N-morpholino)propanesulfonic acid (MOPS) buffers may be used for bis-Tris gels. The buffers in this system should be efficient for both the electrophoresis phase and transfer phase. The tank apparatus 30 has an upper chamber 34 and a lower chamber 36. A first separation phase negative electrode (cathode) 38 is disposed within the upper chamber 34. A second separation phase positive electrode (anode) 40 is disposed within the lower chamber 36. The first and second separation phase electrodes 38, 40 are each connected to a programmable power source (not depicted) to power the separation electrodes 38, 40. Power sources for tank apparatuses for use in electrophoresis and blotting are well known in the art. The desired voltage between the first and second separation phase electrodes 38, 40 is between 80 and 150 volts. The power source employs switching means for electrical isolation of said separation phase electrodes 38, 40 from said blotting transfer electrodes 50, 52.

The upper chamber 34 and lower chamber 36 are each filled with a buffer solution 56 and are electrically connected to each other via the electrically conducting gel/membrane combination unit 10, which allows negative charges to pass from the first separation electrode 38, through the buffer 56 in the upper chamber 34, through gel 6 to buffer 56 in the lower chamber 36 to the second separation electrode 40. This is accomplished in part due to the conductive polymers housing the gel having higher resistance than the gel they house. The rear panel 68 has one or more openings 74 in its lower region to allow the buffer solution 56 from the lower chamber 36 to fill up to the lower surface 18 of the gel 6 to provide an electrical connection from the second separation electrode 40 to the gel 6. The buffer solution 56 in the upper chamber 34 and lower chamber 36 may be the same buffer solution, or may be different buffer solutions, where in some embodiments, the buffer solution 56 in the upper chamber 34 may include an antioxidant.

The wires electrify the buffer solution 56 causing the solution in the upper chamber 34 to act as the cathode (−) and solution in the lower chamber 36 to act as the anode (+). Proteins in a sample buffer containing sodium dodecyl sulfate (SDS), or other buffers that are well known in the art, impart proteins with negative net charge so that when they are in the gel 6, they move from the cathode (−) 38 to the anode (+) 40 by the electromotive force (EMF) created from the power source, as known in the art. By placing proteins in wells 84 in the gel and applying an electric field, the proteins will move through the gel 6 at different rates, determined largely by their mass. Thus, the first separation electrode 38 and second separation electrode 40 act as the cathode and anode, respectively, during the electrophoresis phase that separates proteins and other macromolecules by size.

The buffer solution 56 in the upper chamber 34 and lower chamber 36 are not in liquid contact with each other, but still in electrical contact with each other. The buffer solution 56 in each chamber 34, 36 is prevented from contact by the gel and membrane combination unit 10 and gaskets 44, 46 that prevent the buffer solution 56 from filling the entirety of the tank apparatus 30. A rear panel gasket 46 is disposed on the inner surface of the rear panel 68 of the tank apparatus 10. The rear panel gasket 46 prevents buffer 56 from contacting a blotting electrode 52, which would cause unwanted electrical current flow during the separation phase. Additionally, there is a lip gasket 44 disposed along the outer surface of the lip 58. The lip gasket 44 prevents buffer solution 56, necessary for the separation phase, from contacting the cooling solution 54 used in the cooling chamber 42. The cooling chamber can be filled with water, buffer, or other type of coolant. Gaskets in the preferred embodiments are made from rubber, silicone, or other materials commonly known in the art that form seals that prevents liquid seepage.

Figure 4:
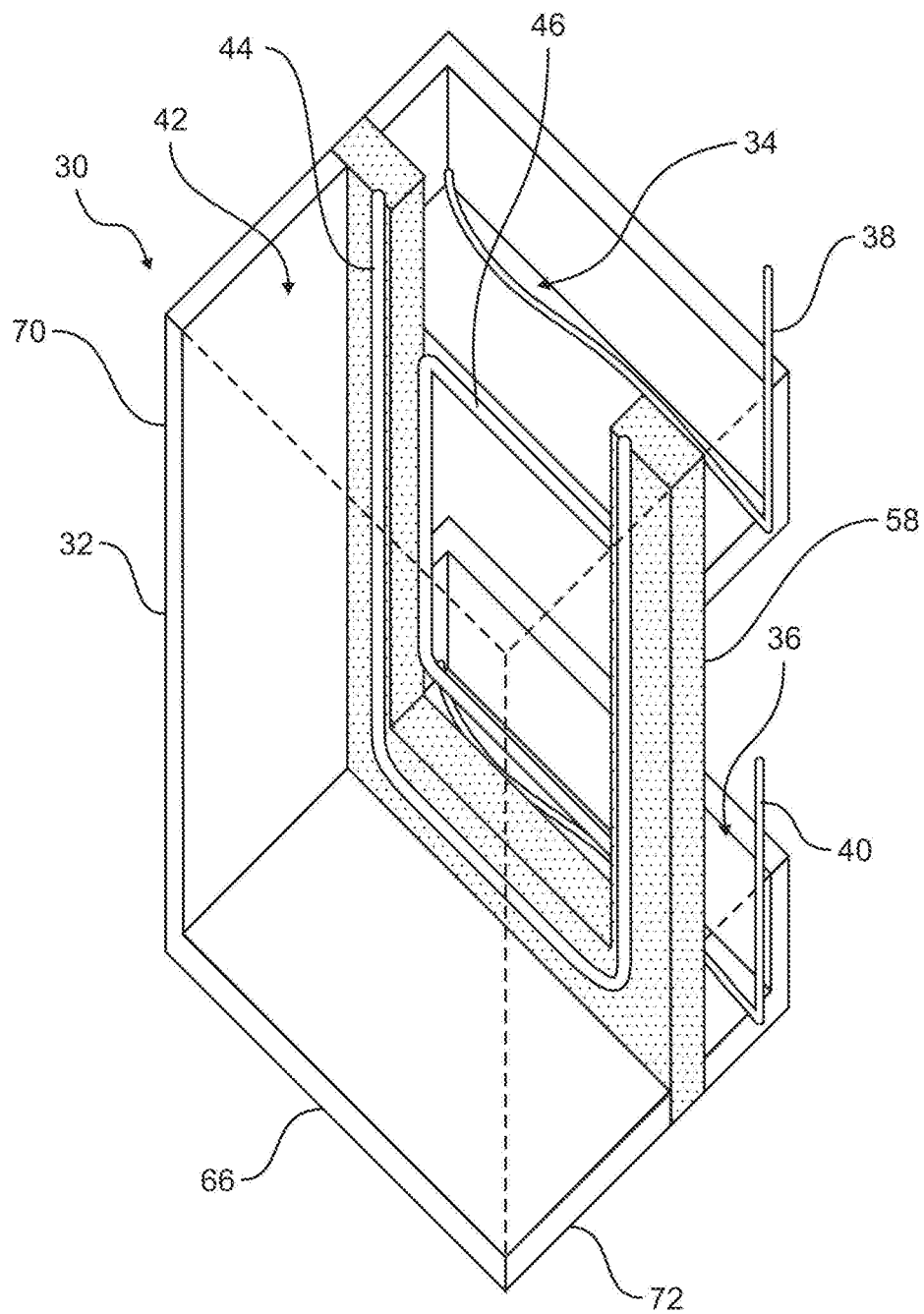
FIG. 4 shows a perspective view of the electrophoresis and transfer tank without the precast gel and membrane combination unit placed inside the tank.

The rear panel gasket 46 is positioned so that when the precast gel and membrane combination unit 10 is placed within the tank apparatus 30, the outer surface 24 of the second conductive plate 4 contacts and is pressed against the gasket 46. The lip gasket 44 is positioned so that the inner surface of the first conductive plate 2 is pressed against the lip gasket 44. As shown in FIG. 4, the rear panel gasket 46 is a continuous loop along the inner surface of the rear panel 68. The lip gasket 44 is an open shape having a bottom region connected to two side regions (with no top region to form a loop gasket). The lack of a rubber sealing structure on the top allows the buffer 56 to be in electrical contact with the top 20 of gel 6. In sum, the gaskets 44, 46 are positioned such that when the precast gel/membrane combination unit 10 is placed correctly within the tank apparatus 10, the gaskets 44, 46 form seals that keep the upper chamber 34 and lower chambers 36 (necessary for the electrophoresis phase) separate from the cooling chamber 42 and other structures required during the protein transfer phase. Another feature to prevent the chambers 34, 36, 42 from being in liquid and/or electrical contact with each other is that the first conductive plate 2 is larger than the second conductive plate 4. In a preferred embodiment, the first conductive plate is approximately 12 cm×12 cm and the second conductive plate 4 is approximately 10 cm×10 cm (approximately the same dimensions of the gel 6). The larger first conductive plate 2 allows for the first conductive plate 2 to contact the lip gasket 44 and the smaller second conductive plate 4 to be in contact with the rear panel gasket 46. The smaller second conductive plate 4 allows the buffer solution 56 to pass over and under the second conductive plate 4 in the upper chamber 34 and lower chamber 36, respectively, to reach the gel 6, but not pass by the larger first conductive plate 2. This prevents the buffer solution 56 from entering into the cooling chamber 42 and contacting the transfer electrodes 50, 52 used during the transfer/blotting phase.

After the separation phase, where the proteins have been separated vertically along the gel 6 due to the electric field created by the upper and lower separation electrodes 38, 40, the electrical current is then shifted from the separation electrodes 38, 40 to transfer electrodes 50, 52 for use in the transfer/blotting phase, which forces the proteins to move from the gel 6 to the membrane 12 via the EMF supplied by the transfer electrodes 50, 52 to the first conductive plate 2 and second conductive plate 4. The first conductive plate 2 is in electrical contact with a first transfer electrode 50 connected to a power source and the second conductive plate 4 is in electrical contact with a second transfer electrode 52. Since the first and second conductive plates 2, 4 are made from conductive plastics, when current is applied to the transfer electrodes 50, 52, the conductive plates 2, 4 act as plate electrodes.

In the embodiment shown in FIG. 3, the first transfer electrode 50 is an arc shaped metal brace to provide sufficient tension to hold the precast gel/membrane combination unit 10 in place against the gaskets 44, 46 to form the different chambers 34, 36, 42. The transfer electrode 50, may also be a separate element from the structure that braces/tensions the precast gel and membrane combination unit 10 inside the tank 30, against the various gaskets 44, 46 within the tank 30. In other embodiments, the first transfer electrode 50 may be separated into two or more brackets (e.g. one on the left side, one on the right side) so that the user can still view the gel 6, but that the precast gel/membrane combination unit 10 would still be held firmly in place. Other types of braces/brackets/tensioners could also be placed inside the cooling chamber 42 without departing from the spirit of the invention as long as there is tension and electrical contact from the transfer electrode 50 to the first conductive plate.

The second transfer electrode 52 is disposed along the inner surface of the rear panel 68 and acts as the anode (+) during the protein transfer/blotting mode. In the embodiment shown in FIG. 3, the second transfer electrode 52 has a spring or recoil action so that the transfer electrode 52 makes sufficient contact with the second conductive plate 4. In other embodiments, the transfer electrode 52 may be a separate element from an element having the spring or recoil action to help brace the precast gel/membrane combination unit 10 inside the tank 30 against an opposing bracing member. An electrical power source connects the first transfer electrode 50 with the second transfer electrode 52 and is applied to the transfer electrodes 50, 52 such that the first conductive plate 2 acts as the cathode (−) and second conductive plate acts as the anode (+) during the transfer/blotting phase. The electrical source shall provide enough electricity to achieve a voltage difference between the two plate electrodes to achieve sufficient transfer of the proteins toward the second conductive plate 4 to the transfer membrane 12 housed within the precast gel/membrane combination unit 10. A typical voltage applied during the blotting mode is around 30 volts.

FIG. 4 is a perspective view of the tank apparatus 30 without the precast gel/membrane combination unit 10. The precast gel/membrane combination unit 10 is placed adjacent to (on the left side) of the lip 58 having the lip gasket 44. Since the first conductive plate 2 is larger than the second conductive plate 4, the first conductive plate 2 lays on the outer surface, while the electrophoresis gel 6, low conductivity gel 8, transfer membrane 12 and filter paper 60 are within the inner cavity of the lip 58 and the second conductive plate 4 is pressed against the rear panel gasket 46.

Figure 5:
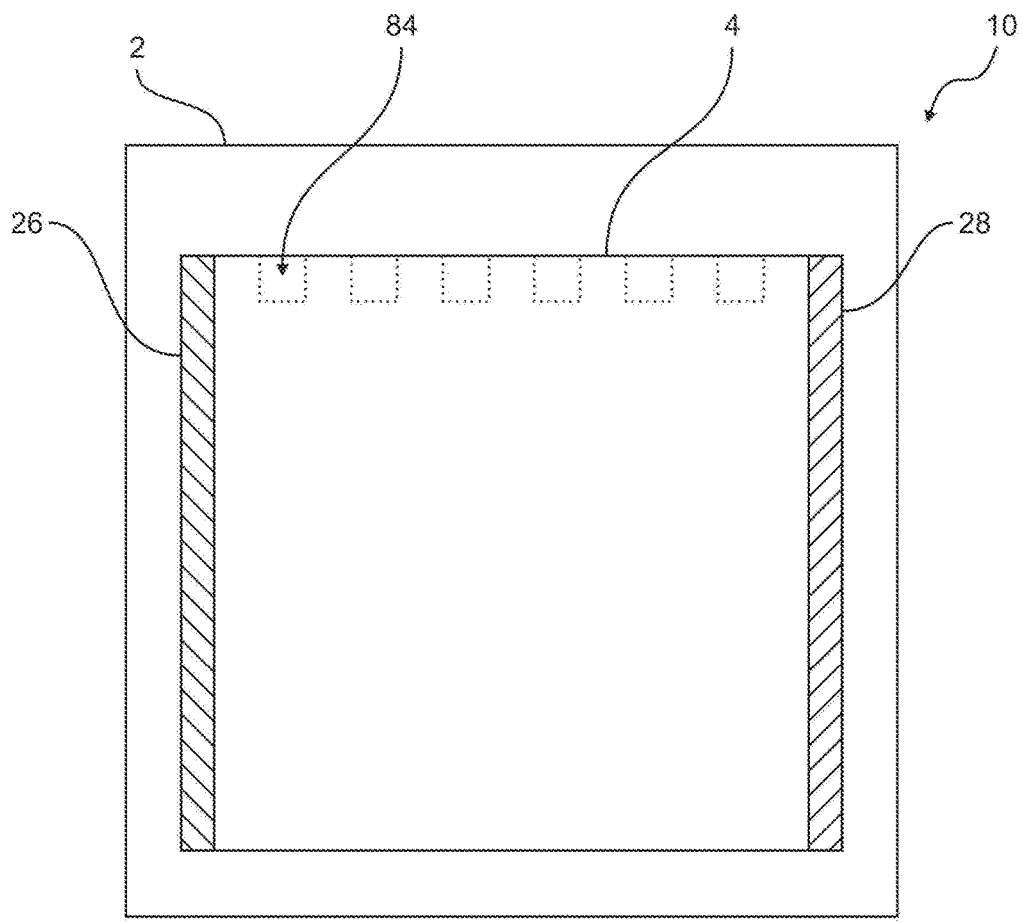
FIG. 5 shows a front view of an embodiment of the precast gel and membrane combination unit.

FIG. 5 is a front view of the precast gel/membrane combination unit 10. As described earlier, the first conductive plate 2 is larger than the second conductive plate 4. The gel 6, low conductivity gel 8, transfer membrane 12, and filter paper 60 (not seen in FIG. 5, as they are blocked by the second conductive plate 4), are all sandwiched between the first and second conductive plates 2, 4. In the embodiment of FIG. 5, the gel 6, low conductivity gel 8, transfer membrane 12, and filter paper 60 have approximately the same height, but may have a slightly smaller width to allow for the insertion of the insulative plastic strips 26, 28, that flank the sides of the gel 6. Wells 84 within the gel 6 may be created by a gel comb during formation of the gel where proteins can be deposited.

Figure 6:
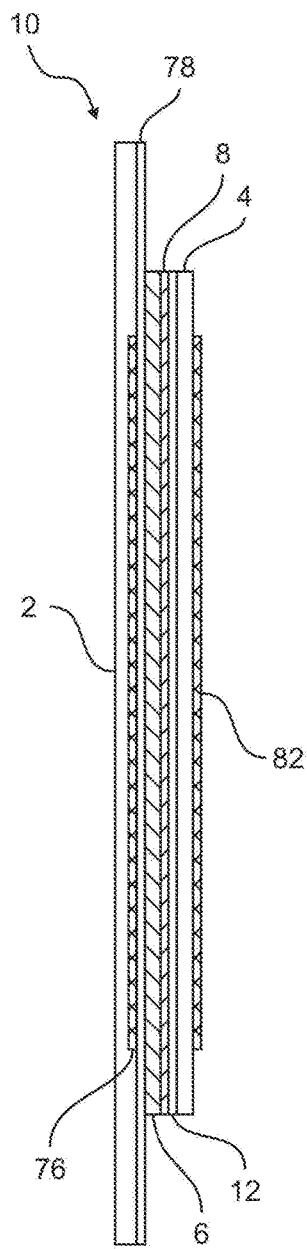
FIG. 6 shows a side view of an embodiment of the gel and membrane combination unit having a conductive wire mesh and thin conductive polymer or film in contact with electrophoresis gel.
Figure 7:
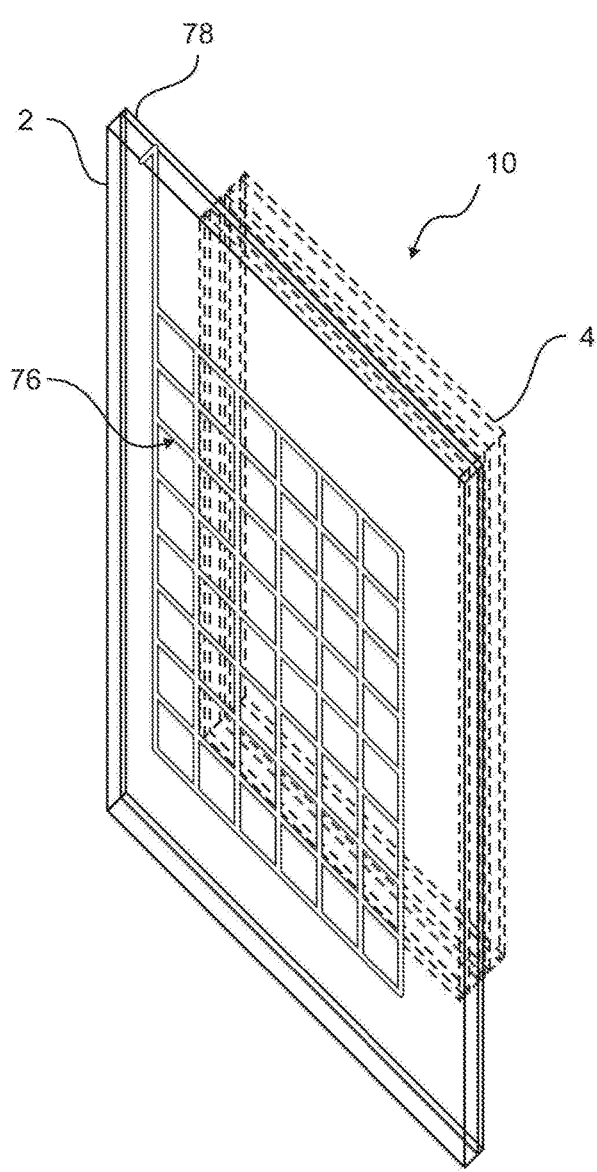
FIG. 7 shows a perspective view of an embodiment of the gel and membrane combination unit.

FIGS. 6-7 show another embodiment of a precast gel/membrane combination unit 10. Instead of the first plate 2 being made entirely from a conductive polymer, the first plate is made from a clear plastic having static dissipative properties, with volume resistivity in the range of approximately $10^8$ to $10^{10}$ ohm-cm. On the inside surface of the first plate 2 or embedded within the first plate 2 are a plurality of conductive wires or mesh 76, which may be arranged in a grid or array. The mesh 76 distributes electric current along the inner surface of the first plate 2. Also disposed along the inner surface of the first plate 2, and in electrical contact with the mesh 76 is a thin transparent conductive layer 78, which may be made from a thin transparent conductive polymer or transparent conducting film (TCF) 78 having a volume resistivity in the range of approximately $10^4$ to $10^5$ ohm-cm. TCFs are known in the art, and in the embodiments of FIGS. 6-7, the first plate 2 is coated with the TCF film 76 or layer of transparent conductive polymer, thereby forming a plate electrode. The wire mesh 76 ensures that electric charge is evenly spread along the film 78 or thin transparent conductive polymer. The TCF may be a conductive polymer but can also be a transparent conducting metal, including, but not limited to indium tin oxide (ITO), fluorine doped tin (FTO), doped zinc oxide, aluminum-doped zinc-oxide (AZO). In a preferred embodiment, the TCF is ITO, as it is chemically resistant to moisture, which is advantageous for long-term storage of the precast gel and membrane combination unit 10.

One possible advantage of a system using TCFs of a thin coat of a transparent conductive polymer is that the transparency of a conductive polymer is reduced as thickness increases, even among known transparent conductive polymers. By limiting the conductive region of the first rigid conductive plate 2 to a thin region of the plate (or layered on top of the plate 2), the gel and membrane combination unit 10 maintains high transparency and high rigidity to form the structural support of an electrophoresis gel 6. A thin film of indium tin oxide is both transparent and conductive. However if thickness and rigidity are both required (such as in the case of gel supporting plates), thick plates of indium tin oxide lose their transparency, and thus are not ideal for forming the entirety of the conductive plate because the plate would not allow a user to visualize protein separation during electrophoresis. The first electrically semi-conductive plate may be characterized has having an outer electrically semi-conductive transparent layer overlying a static-dissipative plastic. This layer may be very thin (less than 1 mm, or even less than 100 μm).

FIGS. 6-7 shows the side view and perspective views respectively, of the first plate 2, wire mesh 76, TCF or thin transparent conductive polymer 78, electrophoresis gel 6, transfer membrane 12, second plate 4, and an additional wire mesh 76 disposed on the outside surface 24 of the second plate 4. The wire mesh 76 disposed along the outside surface of the second 4 efficiently distributes electrical current along the rear plate 4 to more efficiently transfer macromolecules from the gel 6 to the transfer membrane 12.

Figure 8:
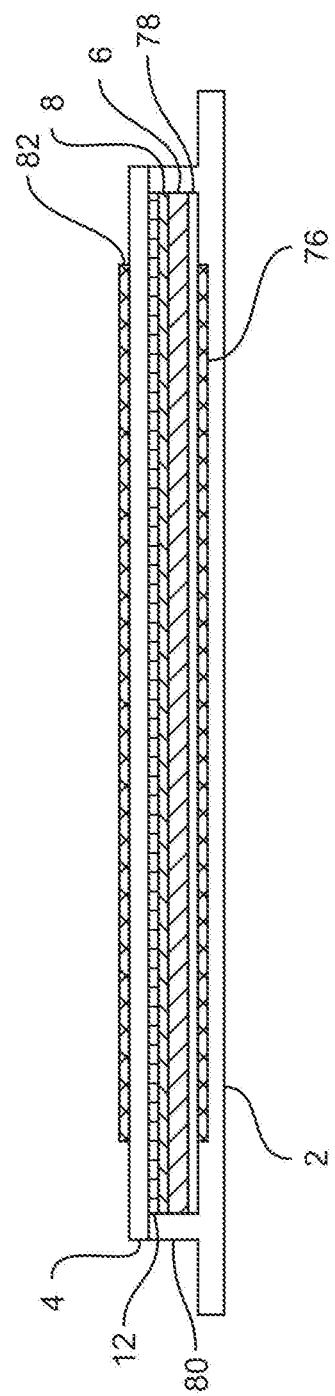
FIG. 8 shows a top view of an embodiment of the gel and membrane combination unit having projections on one plate to create a gap for the gel and membrane.
Figure 9:
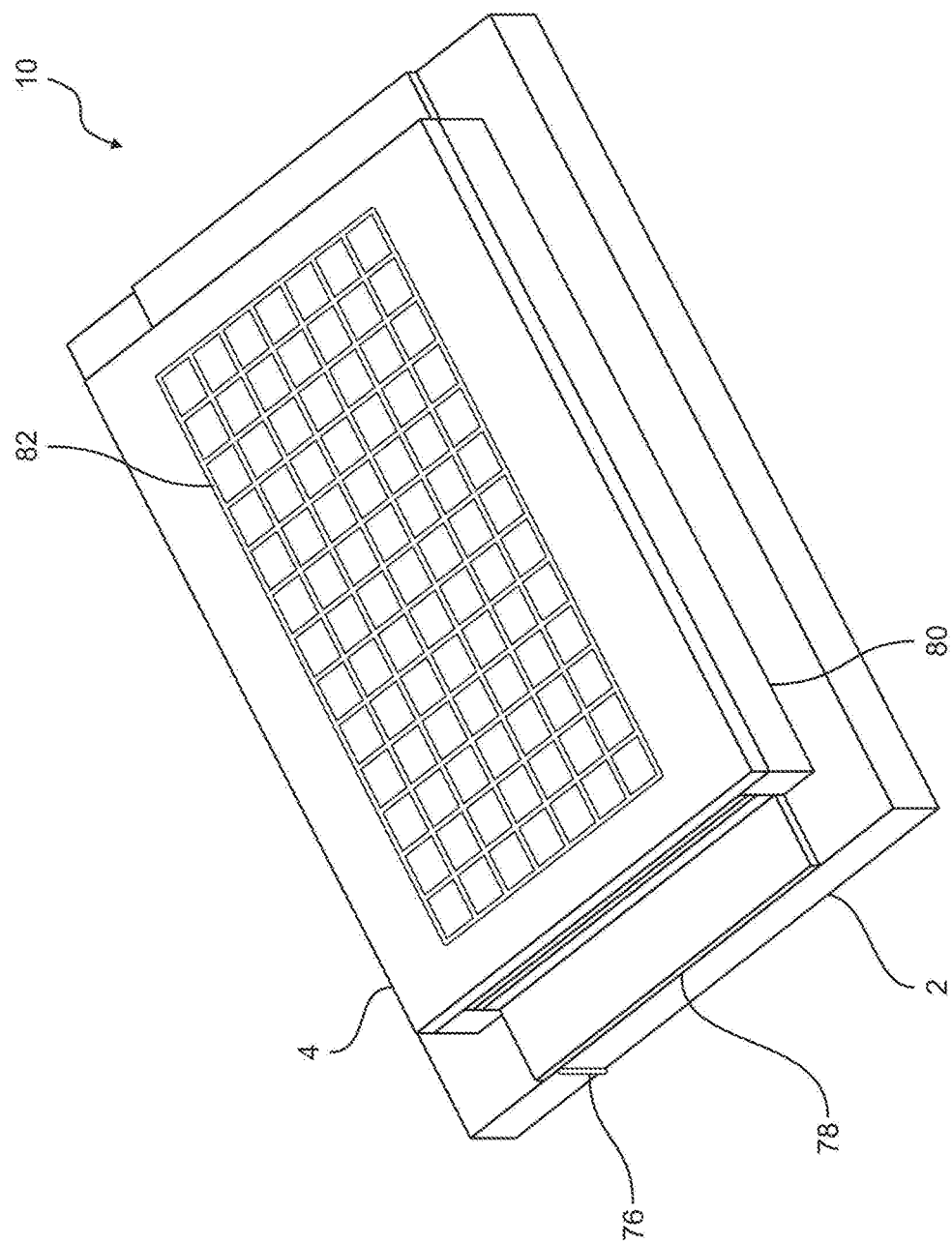
FIG. 9 shows a perspective view of the embodiment of FIG. 8.

FIGS. 8-9 illustrate another example of the precast gel and membrane combination unit 10. FIG. 8 is a top view and FIG. 9 is a perspective view of the precast gel/membrane combination unit 10. This embodiment includes two pedestal projections 80 of the non-conducting static dissipative front plate 2 abutting the inner surface of the rear plate 4. The second plate 4 rests over the pedestals 80, thereby forming a gap between the inner surface of the first plate 2 and the inner surface of the second plate 16. The gap may vary depending on the thickness of the gel. In one embodiment, the gap will range from about 0.1 cm to about 0.5 cm. The gap holds the various components needed for proper separation and blotting of macromolecules, as previously described, such as the electrophoresis gel 6, low conductivity gel 8, transfer membrane 12, and filter paper 60. In this embodiment, the entirety of the first plate 2 is transparent but not highly conductive. Conductivity along the inner surface of the first plate is accomplished through the use of a thin conductive polymer layer or other type of transparent conductive film 78, which overlays or is connected to a first wire mesh 76 that does not visually obstruct the view of gel 6 through the first plate 2. The first wire mesh 76 distributes the electric charge substantially evenly along the entirety of the conductive polymer layer 78 so that an electric field is produced on the thin conductive polymer layer 78, which then acts as a plate electrode. In a preferred embodiment, the film or thin transparent polymer has a thickness of less than 1 mm and has a volume resistivity between $10^4$ and $10^5$ ohm-cm. The rear plate 4 has a second wire mesh 82, which creates a substantially even charge along the entirety of the rear plate 4, thereby producing a substantially even electrical field so that macromolecules are efficiently and evenly transferred from the gel 6 to the transfer membrane 12 during the blotting phase.

In a preferred embodiment, the separation/transfer buffer 56 will have a volume resistivity of approximately 10-200 ohm-cm. The conductive plastic front plate 2 and rear plate 4 will have volume resistivities in the range of $10^3$ to $10^5$ ohm-cm. In embodiments using a thin conductive coating or film 78 on the inner surface of the front plate 2, the volume resistivity of the coating or film will be in the range of $10^4$ to $10^5$ ohm-cm, and the front plate 2 will be made of a static-dissipative transparent plastic with a volume resistivity of $10^8$ to $10^{10}$ ohm-cm. These ranges will allow for the electric current to flow through the gel during the separation phase when a power source is applied to separation electrodes 38, 40 rather than through the front and rear plates 2, 4. Then, when the power source is applied to 50 and 52, or to 76 and 52, the electric current will flow substantially perpendicularly to the length of the gel from the front plate 2, through the gels 6, 8 and membrane 12, to the rear plate 4, allowing for the proteins to be embedded on the blotting membrane 12 during the blotting phase. While these ranges have been described in terms of exemplary embodiments, it is to be understood that they are not limiting, whereas any embodiment in which the buffer 56 and gel 6 have a reasonably lower resistivity than the conductive polymers (i.e. plates 2, 4) that house them, and conversely that the conductive polymers (i.e. plates 2, 4) have a reasonably higher conductivity than the buffer 56 and gel 6 will allow for the described separation and transfer phases.

Properties of Conductive/Semi-Conductive Polymers for Use in Gel Supporting Plates The term "conductive" as it relates to polymers in the present invention is relative to the lack of electrical conductivity found in most polymers, which are insulative. Conductive polymers are less conductive than metals and therefore are semi-conductive, but the term "conductive polymer" is still generally used and refers to all polymers that fall within the range typically regarded as semi-conductive. Polypyrroles typically have conductivity between $10^3$-$7.5\times10^5$ S/m. Polythiophenes have conductivity between $10^1$-$10^3$ S/m. Polyphenylene and its analogs poly(paraphenylene) have conductivity between $10^4$-$10^5$ S/cm. Poly(p-phenylene vinylene) has conductivity between 3-5×$10^5$ S/m, and polyanilines have conductivity between $3\times10^3$-$2\times10^4$ S/m. Conductivity can increase by adding molecules to p-dope or n-dope the polymer (such as doping with $I_2$, $AsF_5$, Na, K). Un-doped conductive polymers, such as polythiophenes and polyacetylenes, generally have conductivity around $10^{-8}$-$10^{-6}$ S/m. Resistivity, which is also commonly used to describe the characteristics of materials, is the mathematical inverse of conductivity.

The conductivity of conductive polymers is orders of magnitude higher than that of typical insulators, such as glass, which has conductivity between $10^{-11}$ to $10^{-15}$ S/m. Similarly, rubber has a conductivity of about $10^{-14}$ S/m. In contrast to insulators, the conductivity of most metals are orders of magnitude higher than that of conductivity polymers. Silver, copper, gold, aluminum, tungsten, or most other metals, which have a conductivity of approximately $10^6$-$10^7$ S/m. The intermediate conductivity property of conductive polymers allows these conductive polymers to act as insulators or conductors, depending on electrical charge applied to it and the compositions surrounding the conductive polymers. The semi-conductive nature of the plates prevents the plates from contributing to a nullifying electric field, which would occur if the gel supporting plates were highly conductive like metals.

Transparency of the Gel Supporting Plates

The term "transparent" as understood in the art when discussing transparent conductive polymers, not only includes polymers that are 100% optically clear, but also includes polymers that are translucent and allow some light to transmit through the polymer. As the thickness of the transparent conductive polymers increases, some attenuation and spectral absorption occurs, but the polymers still allow a substantial amount of a light to transmit at a magnitude great enough that allows a user to visualize a dye front within the gel through the transparent plate. The term "transparent conductive polymer" or "transparent semi-conductive polymer" therefore includes those polymers and plates made from the polymers that allow sufficient light to transmit through the plate that enables a user to visualize a dye front through the plate.

Example Protocol

Gel Electrophoresis

1. Protein samples (cell lysates, immunoprecipitates, recombinant proteins, etc.) are prepared as follows:
   a. Add 10 µL 4× sodium dodecyl sulfate (SDS) sample buffer [e.g. 250 mM Tris-HCL; 8% SDS; 40% glycerol; 4% β-mercaptoethanol; 50 mM ethylenediaminetetraacetic acid (EDTA); 0.8% w/v bromophenol blue] to 30 µL protein sample.
   b. Incubate samples at 70° C. for 10 min.
2. Approximately 20 µL samples are loaded onto the gel 6 (e.g. 10% polyacrylamide) that is adjacent to a membrane 12 that are together between two conductive/semiconductive plastic plates 2, 4 that comprise the precast gel and membrane combination unit 10.
3. Approximately 10 µL pre-stained protein ladder is loaded onto the gel. As the front plate is transparent, the pre-stained protein ladder can be loaded into any well.
4. The proteins are electrophoretically separated at a constant voltage across the separation phase electrodes 38, 40. The voltage and time used for separation depends on the size of the target protein(s), desired degree of separation of the target protein(s), and the percentage of the gel (e.g. 150 V for 60 min for a 10% polyacrylamide gel). As the front plate is transparent, the user can monitor the relative degree of separation through the front plate by visually assessing the progression of the pre-stained protein ladder and the dye front from the protein samples.

Transferring the Separated Samples onto Membranes

1. The separated proteins are electro-transferred onto the membrane 12 at a constant amperage across the transfer electrodes 50, 52. The amperage and time used depends on the size of the target protein(s) to be transferred (e.g. 500 mA, 30 min). The voltage required to achieve this amperage is higher than that compared to standard transfer devices using metal plate electrodes as the resistance is higher, thus final voltage and amperage will depend on the resistance of the polymer used, and the voltage and amperage capabilities of the power supply.

Probing the Separated and Transferred Samples

1. The precast gel and membrane combination unit 10 is disassembled to remove the membrane with the separated proteins.
2. The membrane is incubated in blocking buffer [e.g. 5% non-fat dry milk in Tris-buffered saline with 1% Tween 20 (TBST)] for 1 hour at room temperature (or alternatively overnight at 4° C.).
3. The membrane 12 is incubated with an appropriate dilution of a primary antibody in blocking buffer (e.g. 1:200-1:1000 for many commercially available antibodies) for 1 hour at room temperature (or alternatively overnight at 4° C.).
4. The membrane 12 is washed three times with TBST, 5 min each.
5. The membrane 12 is incubated with the recommended dilution of conjugated secondary antibody in blocking buffer for 1 hour at room temperature (e.g. 1:5000 for HRP-conjugates at 1 mg/mL).
6. The membrane is washed three times with TBST, 5 min each.
7. For signal development, the substrate manufacturer's recommendations are used.
8. Images are acquired using standard darkroom development techniques for chemiluminescence, or normal image scanning methods for colorimetric detection.

Examples of Semi-Conductive Plate Compositions

Numerous formulations of transparent polymers can be to be used as the gel supporting plates. The transparent conductive/semiconductive polymer plates can be made of poly(pyrrole)s (PPY), polyacetylene, polyanilines (PANi), poly(thiophene)s (PT), poly(3,4-ethylenedioxythiophene) (PEDOT), poly(p-phenylene sulfide (PPS), poly(acetylene)s (PAC), and poly(p-phenylene vinylene) (PPV) and composites thereof. For example, PPY, one of the most well-characterized of the conductive/semi-conductive polymers, has been incorporated into composites with conventional/insulating polymers including acrylic polymers (see "Surface Characterization of Conductive Poly(methyl methacrylate)/Polypyrrole Composites," Journal of Materials Science 35 (2000) 1743-1749), cellulose (see "A Nano cellulose Polypyrrole Composite Based on Tunicate Cellulose," International Journal of Polymer Science, Volume 2013, Article ID 175609), polystyrene (see "Synthesis and Characterization of Nano sized Polypyrrole Polystyrene Composite Particles," Journal of Applied Polymer Science, Vol. 91, 1360-1367 (2004)), polyurethane (see "Polypyrrole composites for shielding applications," Synthetic Metals 151 (2005) 211-217), polydimethylsiloxanes (see "Flexible and Conducting Composites of Polypyrrole and Polydimethylsiloxane," Journal of Applied Polymer Science, Vol. 93, 736-741 (2004)), polyethylene glycol (PEG) (see "Studying the Characteristics of Polypyrrole and its Composites," World Journal of Chemistry 2 (2: 67-74, 2007), and poly(acrylonitrile-co-vinyl acetate (see "Characterization of Conductive Poly(Acrylonitrio-co-Vinyl Acetate Composites: Matrix Polymerization of Pyrrole Derivatives," Fibers and Polymers 2011, Vol. 12, No. 2, 151-158). Importantly, PPy composites have been made with these conventional copolymers wherein the composite materials retain the mechanical and physical properties of the conventional material and the electrical conductivity of the conducting polymer (see "Chemical in situ polymerization of polypyrrole on poly (methyl methacrylate) substrate," Thin Solid Film 515 (2007) 5324-5328). These composites have consistently been made within or below the volume resistivity range required for the transfer phase of the precast gel and membrane combination unit, indicating that a low percentage of PPy in a composite with conventional copolymers has a resistivity sufficiently high for use in separation phase during electrophoresis so that a nullifying field effect would not occur, and sufficient conductivity for the transfer phase to transfer proteins from the gel sandwiched between the plates to the blotting membrane.

Conductivity can be adjusted by varying the amount of monomer initiator concentration added to PPy (see "The Regulation of Osteogenesis Using Electroactive Polypyrrole Films. Polymers, 2016; 8(7): 258). PPy can be mixed with conventional plastics so that the blend can retain the transparency and rigidity of conventional plastics as well as the electrical conductance of the PPy. Composites having 99% polyurethane (a conventional polymer) and 1% PPy-Ni (a PPy nickel composite having semi-conductive properties) have conductivity sufficient for a gel plate to use for both electrophoresis protein separation and blotting (see "Polypyrrole Composites for Shielding Applications," Synthetic Metals 151 (2005) 211-217). A 95% conventional polymer 5% PPy polymer, 2 mm thick (or a 90% conventional polymer, 10% PPy composite 1 mm thick plate) is sufficiently rigid, transparent, and conductive for use in the present embodiments. Variations of ranges of thickness between 0.5 mm to 4 mm, or higher, could also be created to use in the present embodiments, so long as the conventional polymer meets the rigidity and transparency requirements, of which there are many well known and available in art. Composites between 1% and 10% PPy may provide the first electrically semi-conductive plate to have sufficient volume resistivity to act as an insulating plate during the protein separation phase and sufficient conductivity to allow proteins to transfer from the gel to the blotting membrane during protein transfer.

In embodiments where the semi-conductive plates are not comprised of a semi-conductive polymer throughout the entirety of the plate, a layer of PPy can be applied to static-dissipative rigid plastic sheets with a thin wire mesh between the plate and PPy can be used to achieve the same goal. Layers as thin or thinning than 100 μm PPy layer can retain enough transparency to allow visibility of a pre-stained protein ladder and sample loading dye (dye front) when coating a transparent static-dissipative plate.

Another composition for use in transparent semi-conductive plates includes polyaniline (PANT) composites, which are electrochromic and change color/transparency depending on the voltage applied (see "Electrochromic Properties of Polyaniline-Based Hybrid Organic/Inorganic Materials," J. Braz. Chem. Soc., Vol. 27, No. 10, 1847-1857, 2016"). For example, when no voltage is applied to the composite, the PANI composite is transparent yellow. The composite changes to green/blue when a voltage is applied. When using this polymer, the composite will be opaque and have low optical transmittance when the apparatus is running, but when a user turns the voltage off, the user can evaluate the extent of protein separation at any time during the electrophoretic run, and then reapply the current to continue protein separation. Thin layers of PANI can be applied to transparent static dissipative sheets, or PANI can be blended with other polymers to retain the yellow transparency in the no-voltage state at higher thicknesses.

Another class of materials to use when transparency is not required (i.e. for the rear plate, which does not require transparency) is that of mixed ion-electric conductors (MIECs). These materials have both ionic and electrical conductivity. For example, a non-transparent electrically conductive/semiconductive plate that is also an ion conductor can be made of nanofibrillated cellulose-Poly[3,4-ethylenedioxythiophene] (NFC-PEDOT) (See "An Organic Mixed Ion-Electron Conductor for Power Electronics," Advanced Science 2016, 3, 1500305). NFC-PEDOT has electrical properties consistent for use during both the separation and transfer phase, and improves the efficiency of the transfer phase as it also acts act as an ion reservoir. Other non-transparent conductive/semi-conductive polymers that can be used to make the plates include commercially available Tivar® EC, Tecaform® ELS, 30% carbon filled polyether-ether-ketone (PEEK), Tecapeek® ELS. Tempalux® CN conductive polyetherimide (PEI), conductive polyethersulfone (PES CN), Static-Control Kynar® PVDF CN (polyvinylidene fluoride), Pomalux® static-control acetal, Propylux® static-control polypropylene, Absylux® static-control acrylonitrile-butadiene-styrene (ABS), and Zelux® static-control polycarbonate, available through Boedeker Plastics, Inc. (Texas)

While the invention has been described in terms of exemplary embodiments, it is to be understood that the words that have been used herein are words of description and not of limitation. As is understood by persons of ordinary skill in the art, a variety of modifications can be made without departing from the scope of the invention defined by the following claims, which should be given their fullest, fair scope.

I claim:

1. An apparatus for electrophoretic separation and blotting, comprising:
    a first electrically semi-conductive plate made from a transparent semi-conductive polymer;
    a second electrically semi-conductive plate made from a semi-conductive polymer, the second electrically semi-conductive plate substantially parallel to the first electrically semi-conductive plate;
    an electrophoresis gel; and,
    a blotting membrane;
    wherein the electrophoresis gel is between the first electrically semi-conductive plate and the blotting membrane; and
    wherein the blotting membrane is between the electrophoresis gel and the second electrically semi-conductive plate.

2. The apparatus of claim 1, further comprising:
    a low conductivity gel having a lower conductivity than the electrophoresis gel, wherein the low conductivity gel is between the electrophoresis gel and the blotting membrane, whereby the low conductivity gel prevents migration of macromolecules from diffusing away from the electrophoresis gel and adhering to the blotting membrane during a macromolecule separation phase;
    a filter paper between the second semi-conductive plate and the blotting membrane, whereby the filter paper, when wet, acts as an ion reservoir and provides substantial electrical contact between the blotting membrane the second semi-conductive plate to aid in transferring macromolecules from the electrophoresis gel through the low conductivity gel to the blotting membrane;
    wherein the blotting membrane is at least one of a nitrocellulose membrane, polyvinylidene difluoride (PVDF) membrane, or nylon membrane.

3. The apparatus of claim 1, further comprising electrically conducting wires disposed on or within the first electrically semi-conductive plate, wherein the first electrically semi-conductive plate is characterized as having an outer electrically semi-conductive transparent layer overlaying a static-dissipative plastic.

4. The apparatus of claim 3, wherein the outer electrically semi-conductive transparent layer is less than 1 mm and disposed on an inner surface of the first electrically semi-conductive plate, wherein the outer electrically semi-conductive transparent layer comprises at least one of indium tin oxide, fluorine doped tin, doped zinc oxide, and aluminum-doped zinc-oxide.

5. The apparatus of claim 1, wherein the first electrically semi-conductive plate is made from a polymer comprising one or more types of transparent conducting polymers selected from the group consisting of polyacetylene, poly(pyrrole)s (PPy), polyanilines, polythiophene, poly(3,4-ethylenedioxythiophene), poly(p-phenylene) sulfide, poly(p-phenylene vinylene), and their derivatives, and wherein the first electrically semi-conductive plate has a volume resistivity between $10^3$ and $10^8$ ohm-cm.

6. The apparatus of claim 5, wherein the first electrically semi-conductive plate has a thickness of at least 1 mm and is comprised of a composite of a transparent conducting polymer and a non-conducting transparent polymer.

7. The apparatus of claim 6, wherein the composite is between 1% and 10% PPy composite, thereby providing the first electrically semi-conductive plate to have sufficient volume resistivity to act as an insulating plate during a protein separation phase and sufficient conductivity to allow proteins to migrate to the blotting membrane during a protein transfer phase, and sufficient rigidity to support the electrophoresis gel, and sufficient transparency to allow a user to visualize a dye front through the first electrically semi-conductive plate.

8. The apparatus of claim 7, wherein the PPy composite is PPy nickel composite having semi-conductive properties.

9. An apparatus for electrophoretic separation and blotting macromolecules, comprising:
    a first plate made of a transparent polymer;
    an electrically semi-conductive transparent layer adjacent to the first plate;
    a second plate substantially parallel to the first plate;
    an electrophoresis gel; and,
    a blotting membrane;
    wherein the electrophoresis gel is between the electrically semi-conductive transparent layer and the blotting membrane; and,
    wherein the blotting membrane is between the electrophoresis gel and the second plate.

10. The apparatus of claim 9, further comprising:
    a first electrically conductive wire array in contact with first plate and the electrically semi-conductive transparent layer; and,
    whereby the first electrically conductive wire array distributes charge along the electrically semi-conductive transparent layer.

11. The apparatus of claim 10, wherein the electrically semi-conductive transparent layer is an electrically conductive film disposed on an inner surface of the first plate, wherein the electrically semi-conductive film is made of a film containing one or more types of conductive transparent metals selected from the group consisting of indium tin oxide, fluorine doped tin, doped zinc oxide, aluminum-doped zinc-oxide, and their derivatives.

12. The apparatus of claim 9, wherein the first plate is made from a polymer containing one or more types of transparent conducting polymers selected from the group consisting of polyacetylene, poly(pyrrole)s (PPy), polyanilines, polythiophene, poly(3,4-ethylenedioxythiophene), poly(p-phenylene) sulfide, poly(p-phenylene vinylene), and their derivatives.

13. The apparatus of claim 9, wherein the transparent conductive layer has a volume resistivity between $10^4$ and $10^5$ ohm-cm and the first plate has a volume resistivity between $10^8$ and $10^{10}$ ohm-cm.

14. The apparatus of claim 9, further comprising a second electrically conducting wire array adjacent to the second plate, whereby the second electrically conducting wire array distributes electrical charge along the second plate.

15. A system for both electrophoretic separation and blotting macromolecules, comprising:
    a liquid receptacle tank having an upper buffer chamber and a lower buffer chamber, a front panel, rear panel, and bottom;

a first separation phase electrode in the upper buffer chamber;

a second separation phase electrode in the lower buffer chamber;

a first blotting phase electrode;

a second blotting phase electrode;

a precast gel and membrane combination unit having (i) a first electrically semi-conductive plate made from a transparent conductive polymer, (ii) a second electrically semi-conductive plate made from a conductive polymer, the second electrically semi-conductive plate substantially parallel to the first electrically conductive plate, (iii) an electrophoresis gel, and (iv) a blotting membrane; and, a power supply, wherein the power supply is configured to apply a voltage to the first separation phase electrode and second separation phase electrode to perform electrophoretic separation of macromolecules along the electrophoresis gel, and wherein the power supply is configured to automatically switch a voltage from the first and second separation phase electrodes to the first and second blotting phase electrodes, whereby switching the voltage allows a user to perform electrophoretic separation of proteins and transfer of proteins onto the blotting membrane.

16. The system of claim 15, wherein the liquid receptacle tank further comprises a cooling chamber housing the first blotting phase electrode; and, a gasket disposed on the rear panel of the liquid tank receptacle, whereby the gasket prevents liquid from flowing from the upper chamber to the lower chamber when the precast gel and membrane combination unit is placed within the liquid receptacle tank.

17. A method for separation and post-separation transfer of macromolecules to a blotting membrane, the method comprising the steps of:

providing an apparatus in a first orientation within a liquid receptacle tank, wherein the apparatus has a first electrically semi-conductive plate made of (i) a transparent semi-conductive polymer, (ii) second electrically semi-conductive plate made of a semi-conductive polymer, the second electrically semi-conductive plate substantially parallel to the first electrically semi-conductive plate, (iii) an electrophoresis gel, and (iv) a blotting membrane, wherein the electrophoresis gel is between the first semi-conductive plate and the blotting membrane, and wherein the blotting membrane is between the electrophoresis gel and the second electrically semi-conductive plate;

separating macromolecules along the gel of the apparatus by applying a first electrical driving force to a pair of separation electrodes, wherein separating macromolecules along the gel occurs in the first orientation of the apparatus;

discontinuing the first electrical driving force to the pair of separation electrodes;

transferring macromolecules through the gel to the blotting membrane by applying a second electrical driving force substantially perpendicular to the first electrical driving force while maintaining the first orientation of the apparatus, thereby combining the steps of macromolecule separation and transfer to a blotting membrane in a single liquid receptacle tank without having to reorient the apparatus between the separating step and transferring step.

18. The method of claim 17 further comprising the step of:

pre-programming a power source to apply the first electrical driving force, discontinue the first electrical driving force, and apply the second electrical driving force substantially perpendicular to the first electrical driving force.

\* \* \* \* \*